US010646296B2

(12) United States Patent
Hasegawa et al.

(10) Patent No.: US 10,646,296 B2
(45) Date of Patent: May 12, 2020

(54) MEDICAL MANIPULATOR SYSTEM, CONTROLLER, AND COMPUTER-READABLE STORAGE DEVICE

(71) Applicant: OLYMPUS CORPORATION, Tokyo (JP)

(72) Inventors: Mitsuaki Hasegawa, Tokyo (JP); Takumi Isoda, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 103 days.

(21) Appl. No.: 15/976,099

(22) Filed: May 10, 2018

(65) Prior Publication Data

US 2018/0256273 A1 Sep. 13, 2018

Related U.S. Application Data

(63) Continuation of application No. PCT/JP2016/051672, filed on Jan. 21, 2016.

(51) Int. Cl.
*A61B 34/37* (2016.01)
*A61B 34/00* (2016.01)
(Continued)

(52) U.S. Cl.
CPC .............. *A61B 34/70* (2016.02); *A61B 34/37* (2016.02); *A61B 34/74* (2016.02); *B25J 9/06* (2013.01);
(Continued)

(58) Field of Classification Search
CPC ............. A61B 34/70; A61B 34/37; B25J 9/06
(Continued)

(56) References Cited

U.S. PATENT DOCUMENTS

2002/0082612 A1* 6/2002 Moll ...................... A61B 34/30 606/130
2011/0245844 A1 10/2011 Jinno
(Continued)

FOREIGN PATENT DOCUMENTS

EP 3 326 565 A1 5/2018
JP 2009-520573 A 5/2009
(Continued)

OTHER PUBLICATIONS

International Search Report dated Apr. 12, 2016 received in PCT/JP2016/051672.

(Continued)

*Primary Examiner* — Kawing Chan
(74) *Attorney, Agent, or Firm* — Scully, Scott, Murphy & Presser, P.C.

(57) ABSTRACT

A medical manipulator system having: an end effector configured to be controlled to perform a treatment; an arm to which the end effector is attached, wherein the arm has a plurality of movable parts, wherein the plurality of movable parts are configured to be moved under one of a plurality of modes, wherein each of the plurality of modes comprises a combination of: movement by one or more actuators; and movement by an external force; and a controller configured to: control the end effector to perform the treatment; and select the one of the plurality of modes; and effect movement of the plurality of movable parts by controlling the one or more actuators and by permitting movement by the external force in accordance with the one of the plurality of modes selected.

15 Claims, 6 Drawing Sheets

(51) Int. Cl.

| | |
|---|---|
| ***B25J 9/16*** | (2006.01) |
| ***B25J 9/06*** | (2006.01) |
| *A61B 90/00* | (2016.01) |
| *A61B 17/00* | (2006.01) |
| *A61B 34/30* | (2016.01) |

(52) U.S. Cl.

CPC ... *B25J 9/1676* (2013.01); *A61B 2017/00477* (2013.01); *A61B 2017/00973* (2013.01); *A61B 2034/302* (2016.02); *A61B 2090/0811* (2016.02); *A61B 2090/08021* (2016.02); *G05B 2219/45117* (2013.01)

(58) Field of Classification Search

USPC .................................................... 318/568.11

See application file for complete search history.

(56) References Cited

U.S. PATENT DOCUMENTS

| | | | |
|---|---|---|---|
| 2013/0325031 | A1 | 12/2013 | Schena et al. |
| 2014/0052153 | A1 | 2/2014 | Griffiths et al. |
| 2014/0222023 | A1 | 8/2014 | Kim et al. |
| 2014/0276953 | A1 | 9/2014 | Swarup et al. |
| 2014/0343369 | A1 | 11/2014 | Nakamura et al. |

FOREIGN PATENT DOCUMENTS

| | | | |
|---|---|---|---|
| JP | 2011-206312 | A | 10/2011 |
| JP | 2013-510632 | A | 3/2013 |
| JP | 2014-204794 | A | 10/2014 |
| JP | 2015-23884 | A | 2/2015 |
| WO | 2006/124390 | A2 | 11/2006 |
| WO | 2007/075864 | A1 | 7/2007 |
| WO | 2011/058530 | A1 | 5/2011 |
| WO | 2013/018936 | A1 | 2/2013 |

OTHER PUBLICATIONS

Extended Supplementary European Search Report dated Aug. 20, 2019 in European Patent Application No. 16 88 6317.3.

* cited by examiner

FIG. 4

| | | FIRST MANIPULATION UNIT | | |
|---|---|---|---|---|
| | | MANIPULATION IS BEING PERFORMED | | NO MANIPULATION IS BEING PERFORMED |
| | | CONSTRAINING ONLY REMOTE CENTER POSITION | CONSTRAINING BOTH REMOTE CENTER POSITION AND END EFFECTOR POSITION | |
| MODE CHANGE INPUT UNIT | INPUT | FIRST MODE | SECOND MODE | THIRD MODE |
| | NO INPUT | FOURTH MODE | | |

MEDICAL MANIPULATOR SYSTEM, CONTROLLER, AND COMPUTER-READABLE STORAGE DEVICE

CROSS-REFERENCE TO RELATED APPLICATIONS

This application is a continuation application of PCT International Application No. PCT/JP2016/051672, filed on Jan. 21, 2016. The content of PCT International Application No. PCT/JP2016/051672 is incorporated herein by reference.

BACKGROUND

Field

The present invention relates to a medical manipulator system.

Description of Related Art

Conventionally, a medical manipulator system which performs a surgical operation by operating a plurality of arms is known. For example, US Patent Application Publication No. 2013/325031 discloses a medical manipulator system that has a plurality of arms to which surgical instruments are attachable, and the medical manipulator system can move the arms such that the surgical instruments are swung about an incision position as a center (a remote center), wherein the incision position is set for introducing the surgical instruments into the body.

According to the medical manipulator system disclosed in US Patent Application Publication No. 2013/325031, it is possible that link mechanisms of the arms are automatically or manually moved while maintaining the position of the remote center.

SUMMARY

According to a first aspect of the present invention, a medical manipulator system is provided. The medical manipulator system comprises: an end effector configured to be controlled to perform a treatment; an arm to which the end effector is attached, wherein the arm comprises a plurality of movable parts, and wherein the plurality of movable parts are configured to be moved under one of a plurality of modes, wherein each of the plurality of modes comprises a combination of: movement by one or more actuators; and movement by an external force; and a controller configured to: control the end effector to perform the treatment; and select the one of the plurality of modes; and effect movement of the plurality of movable parts by controlling the one or more actuators and by permitting movement by the external force in accordance with the one of the plurality of modes selected.

According to a second aspect of the present invention, a controller for controlling a medical manipulator system, the medical manipulator system comprising: an end effector configured to be controlled to perform a treatment; and an arm to which the end effector is attached, wherein the arm comprises a plurality of movable parts, and wherein the plurality of movable parts are configured to be moved under one of a plurality of modes, wherein each of the plurality of modes comprises a combination of: movement by one or more actuators; and movement by an external force, is provided. The controller comprises one or more processors configured to: control the end effector to perform the treatment; and select the one of the plurality of modes; and effect movement of the plurality of movable parts by controlling the one or more actuators and by permitting movement by the external force in accordance with the one of the plurality of modes selected.

According to a third aspect of the present invention, a computer-readable storage device storing instructions for controlling a medical manipulator system, the medical manipulator system comprising: an end effector configured to be controlled to perform a treatment; and an arm to which the end effector is attached, wherein the arm comprises a plurality of movable parts, and wherein the plurality of movable parts are configured to be moved under one of a plurality of modes, wherein each of the plurality of modes comprises a combination of: movement by one or more actuators; and movement by an external force, is provided. The instructions cause a computer to perform processes comprising: controlling the end effector to perform the treatment; and selecting the one of the plurality of modes; and effecting movement of the plurality of movable parts by controlling the one or more actuators and by permitting movement by the external force in accordance with the one of the plurality of modes selected.

BRIEF DESCRIPTION OF DRAWINGS

FIG. 4 is a table showing selection conditions of control modes in the medical manipulator system.

DETAILED DESCRIPTION

First Embodiment

Figure 1:
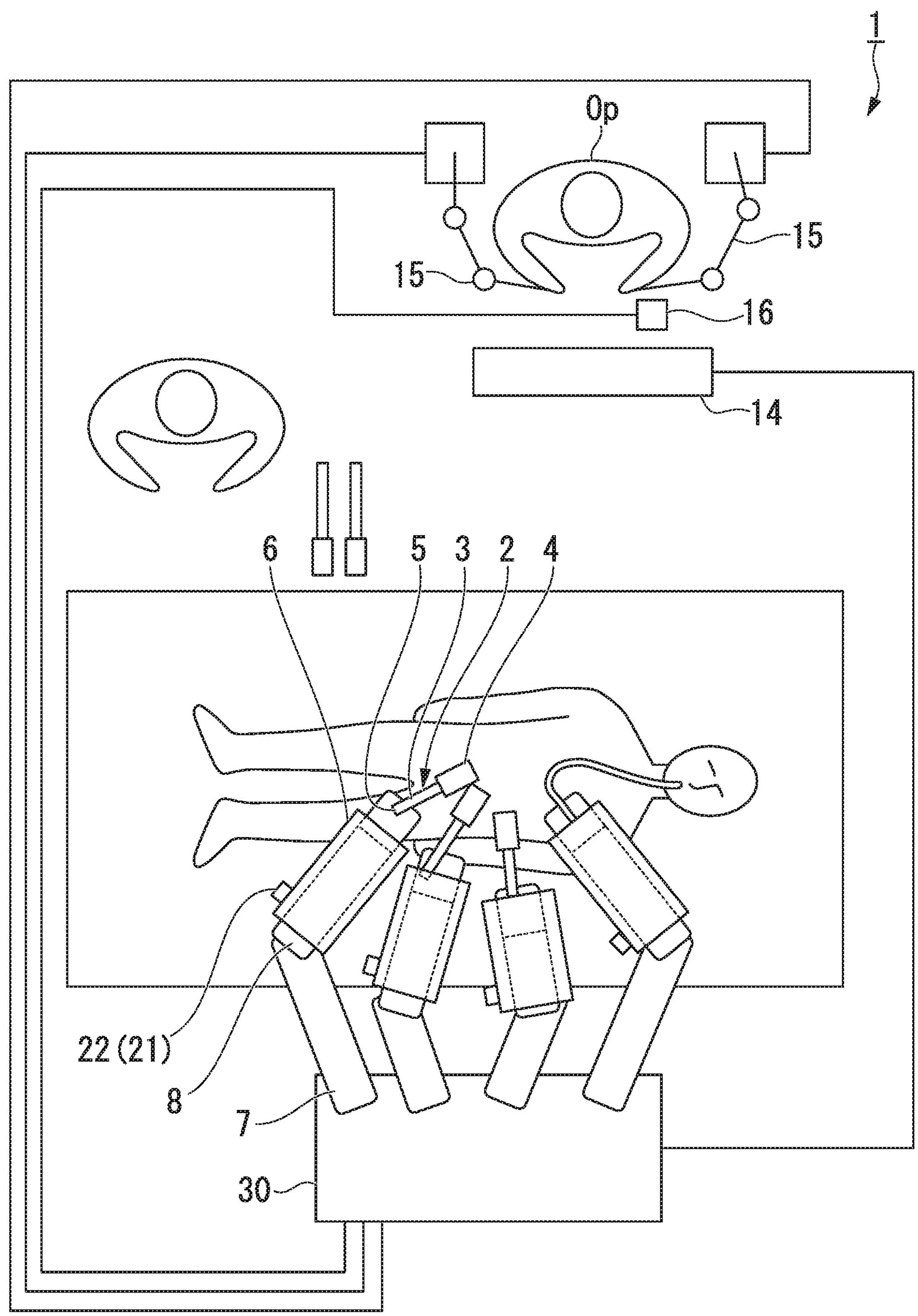
FIG. 1 is a schematic overall view of a medical manipulator system according to a first embodiment of the present invention.
Figure 2:
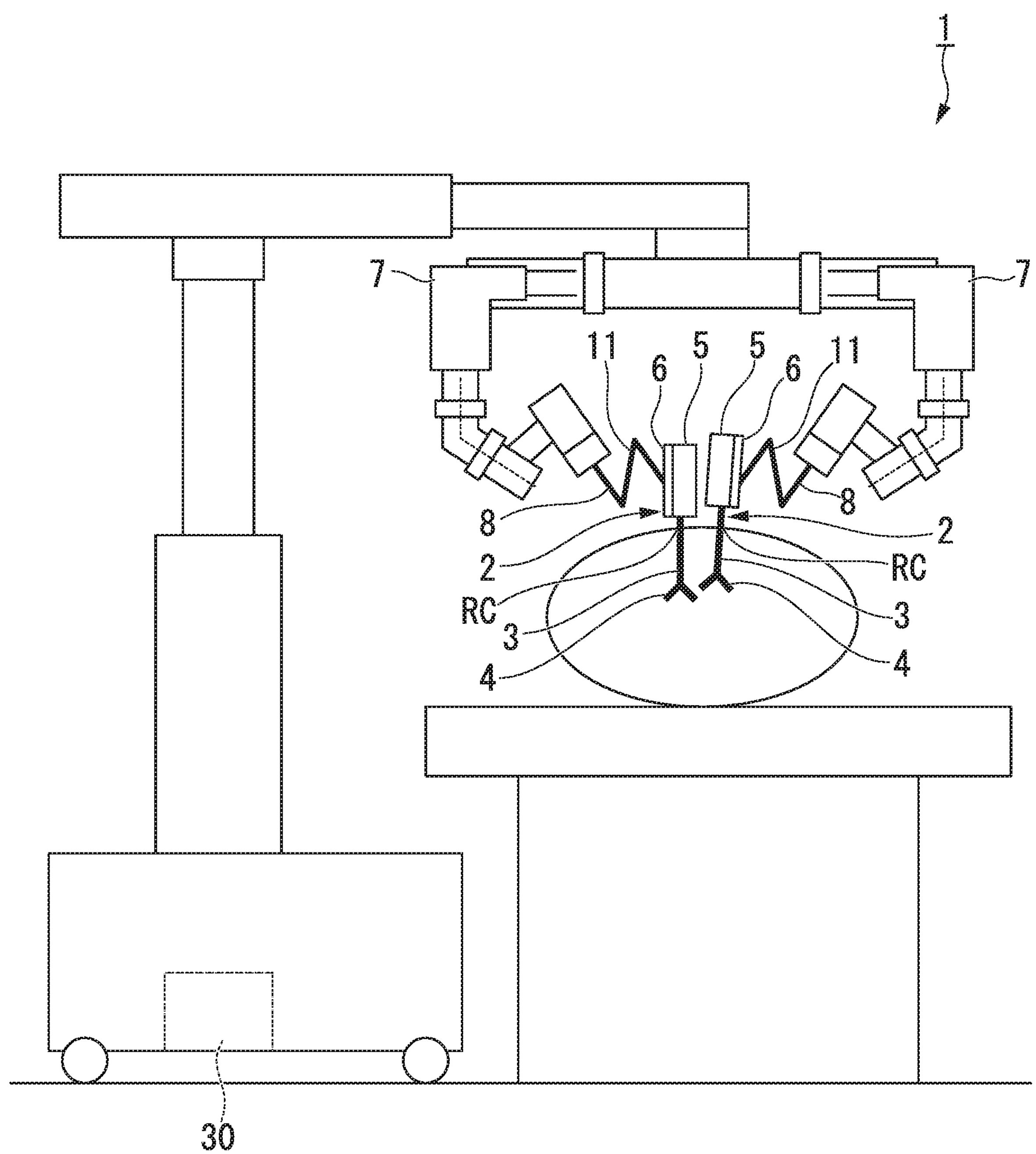
FIG. 2 is a schematic diagram of the medical manipulator system.
Figure 3:
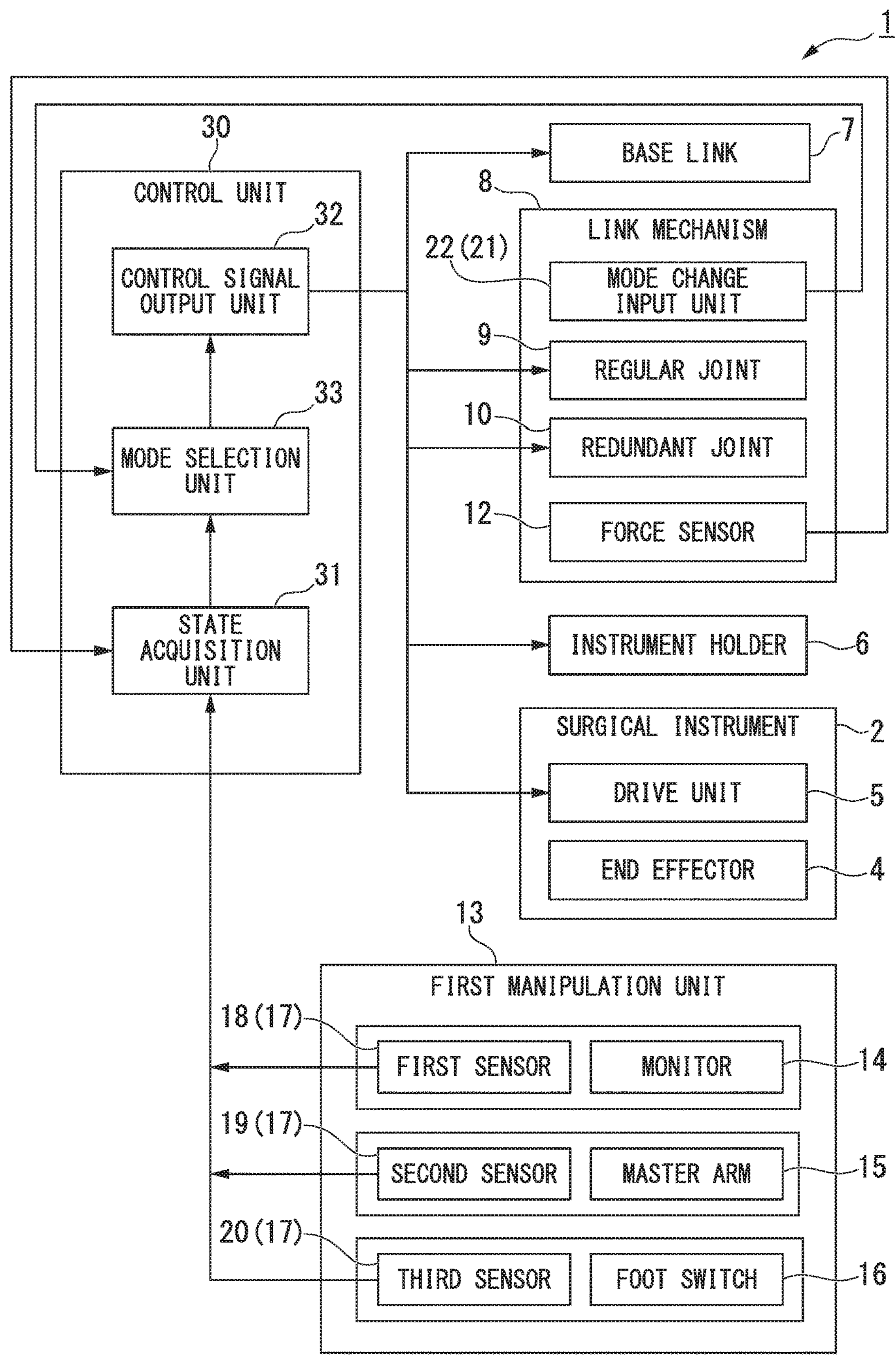
FIG. 3 is a block diagram of the medical manipulator system.

A first embodiment of the present invention will now be described. FIG. 1 is a schematic overall view of a medical manipulator system according to the present embodiment. FIG. 2 is a schematic diagram of the medical manipulator system. FIG. 3 is a block diagram of the medical manipulator system. FIG. 4 is a table showing selection conditions of control modes in the medical manipulator system.

As shown in FIGS. 1 to 3, a medical manipulator system 1 according to the present embodiment includes a surgical instrument 2, an instrument holder 6, a base link 7, a link mechanism 8, a first manipulation unit 13, a second manipulation unit 21, a mode change input unit 22, and a control unit 30 (also referenced throughout this disclosure as controller). In the present embodiment, the medical manipulator system 1 includes a plurality of surgical instruments 2, and a plurality of instrument holders 6 and a plurality of link mechanisms 8 corresponding respectively to the plurality of surgical instruments 2. Instead of a surgical instrument 2, an endoscope may be attached to each of one or some of the plurality of instrument holders 6.

As shown in FIGS. 1 and 2, the surgical instrument 2 includes a shaft 3 insertable into the body, an end effector 4 disposed at a distal end of the shaft 3, and a drive unit 5 disposed at a proximal end of the shaft 3 to operate the end effector 4.

A manipulation of the end effector 4 is controlled by the control unit 30 based on a manipulation on the first manipulation unit 13. A configuration of a known end effector 4 applied to laparoscopic surgery such as, for example, a grasping forceps or a knife may be appropriately selected as a configuration of the end effector 4 of the present embodiment.

The instrument holder 6 is configured to be coupled to the surgical instrument 2. In the present embodiment, the drive unit 5 of the surgical instrument 2 can be attached to the instrument holder 6. For example, the instrument holder 6 transfers a driving force for operating the end effector 4 to the drive unit 5 according to control that the control unit 30 performs based on a manipulation that has been input to the first manipulation unit 13.

The base link 7 is configured to be maintained at a fixed position relative to a patient. For example, the base link 7 is disposed near an operating table.

The link mechanism 8 couples the instrument holder 6 to the base link 7 in a state in which one or more degrees of freedom exists between the instrument holder 6 and the base link 7. The link mechanism 8 includes a joint (a regular joint 9, see FIG. 3) which imparts an indispensable degree of freedom for moving the instrument holder 6 with respect to the base link 7, a joint (a redundant joint 10, see FIG. 3) which imparts a redundant degree of freedom exceeding the indispensable degree of freedom to the link mechanism 8, and a plurality of arms 11 connecting the joints.

The link mechanism 8 further includes a force sensor 12 (see FIG. 3) for detecting that the link mechanism 8 has touched another object. The force sensor 12 of the link mechanism 8 is used, for example, to detect interference between the plurality of link mechanisms 8 and contact, collision, or the like of the link mechanism 8 with a person, other medical instruments, or the like.

As shown in FIGS. 1 and 3, the first manipulation unit 13 includes a monitor 14, master arms 15, the instrument holder 6, and the link mechanism 8, a foot switch 16, and sensors 17. The monitor 14 is provided for displaying an image of a part to be treated. The master arm 15 is provided for manipulating the surgical instrument 2. The foot switch 16 is provided to allow a surgeon to select whether to enable or disable movement of each part based on a manipulation on the master arms 15. The sensors 17 are provided for determining whether or not the surgeon is using the first manipulation unit 13.

The surgeon who uses the first manipulation unit 13 can remotely manipulate the surgical instrument 2, the instrument holder 6, and the link mechanism 8 by manipulating the master arms 15 while viewing an image displayed on the monitor 14 after enabling movements of each part by manipulating the foot switch 16. Manipulations on the master arms 15 include a manipulation of constraining a part of the shaft 3 of the surgical instrument 2 as a remote center RC and moving the end effector 4, and a manipulation of constraining the position of the remote center RC and the position of the end effector 4 and performing a treatment using the end effector 4. The first manipulation unit 13 issues a manipulation command to the control unit 30 based on a manipulation on the master arms 15.

The sensors 17 of the first manipulation unit 13 include a first sensor 18, a second sensor 19, and a third sensor 20. The first sensor 18 is provided for detecting whether or not the head of the surgeon is positioned at an appropriate position to see the monitor 14. The second sensor 19 is provided for detecting whether or not the surgeon is manipulating the master arms 15. The third sensor 20 is provided for detecting the presence or absence of an input to the foot switch 16.

The second manipulation unit 21 shown in FIGS. 2 and 3 is a manipulation unit for manipulating the link mechanism 8. The second manipulation unit 21 in the present embodiment is set on a part of outer surfaces of each arm 11 and each joint of the link mechanism 8. In the present embodiment, the second manipulation unit 21 is configured by a portion which is preset as a portion which the operator (assistant) of the second manipulation unit 21 may touch. In the present embodiment, the operator (assistant) can manipulate the link mechanism 8 by directly pushing and pulling each arm 11 and each joint of the link mechanism 8.

The mode change input unit 22 is provided at a portion of the link mechanism 8 which is set as the second manipulation unit 21. The mode change input unit 22 is used when the operator (assistant) performs a manipulation of directly pushing and pulling the second manipulation unit 21. That is, the mode change input unit 22 is a switch that allows the assistant who manipulates the second manipulation unit 21 to start a manipulation of manually moving the link mechanism 8. In a state in which the assistant does not need to manually change the position or orientation of the link mechanism 8, no input is performed on the mode change input unit 22. When the assistant needs to manually change the position or orientation of the link mechanism 8, the assistant performs an input on the mode change input unit 22.

For example, the mode change input unit 22 of the present embodiment is a push button switch electrically connected to the control unit 30. In the present embodiment, the push button switch of the mode change input unit 22 is on while being pushed and is turned off when the force of pushing the push button switch is released.

The medical manipulator system 1 of the present embodiment has a plurality of mode change input units 22 such that each of the plurality of the mode change input units 22 is arranged on each of the plurality of link mechanisms 8, respectively. A plurality of mode change input units 22 may be arranged on a link mechanism 8.

The control unit 30 shown in FIGS. 1 to 3 controls the base link 7, the link mechanism 8, the instrument holder 6, and the surgical instrument 2 based on the manipulations performed on the first manipulation unit 13 and the second manipulation unit 21.

As shown in FIG. 3, the control unit 30 includes a state acquisition unit 31, a control signal output unit 32, and a mode selection unit 33.

The state acquisition unit 31 acquires a state of the medical manipulator system 1 by referring to the various sensors 17 and the like.

For example, the state acquisition unit 31 refers to the sensors 17 disposed on the first manipulation unit 13 to acquire information indicating whether or not the medical manipulator system 1 is in a state in which a manipulation is being performed using the first manipulation unit 13 as follows.

When the first sensor 18 has detected the head of the surgeon, the state acquisition unit 31 stores the state of the medical manipulator system 1 as a state in which a manipulation is being performed using the first manipulation unit 13.

When the second sensor 19 has detected a manipulation on the master arms 15, the state acquisition unit 31 stores the state of the medical manipulator system 1 as a state in which a manipulation is being performed using the first manipulation unit 13.

When the third sensor 20 has detected the presence of an input to the foot switch 16, the state acquisition unit 31 stores the state of the medical manipulator system 1 as a state in which a manipulation is being performed using the first manipulation unit 13.

That is, the state acquisition unit 31 stores the state of the medical manipulator system 1 as a state in which no manipulation is being performed using the first manipulation unit 13, in a state in which the first sensor 18 has not detected the head of the surgeon, also the second sensor 19 has not detected a manipulation on the master arms 15, and also the third sensor 20 has not detected an input to the foot switch 16.

When any of the foot switch 16, the master arms 15, or the monitor 14 is being used, the state acquisition unit 31 stores the state of the medical manipulator system 1 as a state in which the first manipulation unit 13 is being manipulated. Thus, for example, during a short rest in which the hand is released from the master arms 15 only for a short time, or when the foot switch 16 is merely depressed again, the state of the first manipulation unit 13 is a state in which the first manipulation unit 13 is being manipulated.

The state acquisition unit 31 also refers to the force sensor 12 disposed on the link mechanism 8 to acquire a state of the presence or absence of interference between the plurality of link mechanisms 8. As one example, the state acquisition unit 31 of the present embodiment refers to the force sensor 12 disposed on the link mechanism 8 to acquire a state indicating whether or not the link mechanism 8 has touched another object.

In the present embodiment, when there are simultaneous inputs to the force sensors 12 of the plurality of link mechanisms 8, the state acquisition unit 31 stores a state in which interference occurs between the link mechanisms 8.

When a force sensor 12 of a single link mechanism 8 which is moving has detected contact with another object, the state acquisition unit 31 stores a state in which the link mechanism 8 is in contact with an object other than those recognized by the medical manipulator system 1.

The control signal output unit 32 outputs control signals for operating the surgical instruments 2, the instrument holders 6, the base links 7, and the link mechanisms 8 based on a manipulation command issued by the first manipulation unit 13. The control signal output unit 32 also outputs control signals for operating the link mechanisms 8 based on a manipulation on the second manipulation unit 21.

Control modes set in the control signal output unit 32 will now be described.

A plurality of control modes are set in the control signal output unit 32. The plurality of control modes include a treatment mode (not shown), and link adjustment modes (first to fourth modes shown in FIG. 4). The treatment mode is provided for outputting control signals to the surgical instrument 2, the instrument holder 6, the base link 7, and the link mechanism 8 based on only a manipulation command issued by the first manipulation unit 13. The link adjustment modes are provided for outputting control signals to the surgical instrument 2, the instrument holder 6, the base link 7, and the link mechanism 8 based on both a manipulation command issued by the first manipulation unit 13 and a manipulation on the second manipulation unit 21.

The treatment mode is a mode in which the medical manipulator system 1 (see FIGS. 1 to 3) of the present embodiment operates to perform a treatment. In the treatment mode, the surgical instrument 2, the instrument holder 6, the base link 7, and the link mechanism 8 are automatically controlled according to a manipulation that the surgeon (manipulator) performs using the first manipulation unit 13. The treatment mode is selected by the mode selection unit 33, when the state acquisition unit 31 has acquired a state in which the first manipulation unit 13 is in use and a fourth mode, which will be described later with regard to the second manipulation unit 21, has been selected.

The link adjustment modes are modes for adjusting the position and orientation of the link mechanism 8 when the medical manipulator system 1 of the present embodiment is used. Adjustment of the position and orientation of the link mechanism 8 in the link adjustment modes is performed by an assistant (an operator other than the surgeon) who performs manipulation in the vicinity of the second manipulation unit 21. In the link adjustment modes, the link mechanism 8 operates according to a manipulation that the assistant performs on the second manipulation unit 21.

As shown in FIG. 4, the link adjustment modes include first and second modes, a third mode, and a fourth mode. The first and second modes are provided for allowing the position and orientation of the link mechanism 8 to be adjustable when the medical manipulator system is in a state in which the first manipulation unit 13 is in use, such as when the surgeon is performing a treatment on a part to be treated. The third mode is provided for allowing the assistant to freely operate the surgical instrument 2, the instrument holder 6, the base link 7, and the link mechanism 8 when the medical manipulator system is not in a state in which the first manipulation unit 13 is in use. The fourth mode is provided for prohibiting manipulation on the second manipulation unit 21.

The first mode is a mode for allowing adjustment of the position of the link mechanism 8 while a treatment is performed with the position of the remote center RC (see FIG. 2) being fixed, wherein the remote center RC is a center about which the surgical instrument 2 is allowed to swing. That is, the first mode allows the surgical instrument 2 to be manipulated by the first manipulation unit 13 with the position of the remote center RC being fixed. Also, the first mode allows the link mechanism 8 to be moved by the second manipulation unit 21 while a correspondence relationship between manipulation of the first manipulation unit 13 and movement of the surgical instrument 2 is maintained.

The position of the remote center RC in the first mode is the position of a trocar (i.e., the insertion position of the surgical instrument 2) that is placed in the patient when the shaft 3 of the surgical instrument 2 is inserted into the body of the patient. When a trocar is not used (for example, during a laparotomy operation), the position of the remote center RC may be a desired position that is suitable for surgery.

In the first mode, the shaft 3 can be allowed to swing about the remote center RC. Furthermore, in the first mode, the shaft 3 can be advanced and retracted with respect to the trocar with a part of the shaft 3 being positioned at the remote center RC. Therefore, in the first mode, it is possible to perform control of moving the end effector 4 in the body. The first mode is used for positioning to dispose the end effector 4 in the vicinity of the part to be treated.

The second mode is a mode for allowing adjustment of the position of the link mechanism 8 while a treatment is performed with the position of the end effector 4 of the surgical instrument 2 being fixed. That is, the second mode allows the surgical instrument 2 to be manipulated by the first manipulation unit 13 with the position of the remote center RC and the position of the end effector 4 shown in FIG. 2 being fixed. Also, the second mode allows the link mechanism 8 to be moved by the second manipulation unit 21 while a correspondence relationship between manipulation of the first manipulation unit 13 and movement of the surgical instrument 2 is maintained.

In the second mode, the position of the end effector 4 is fixed in the body and it is possible to perform control of a distal end portion of the surgical instrument 2, such as swinging or opening and closing movement of the end effector 4. The second mode is used to operate the end effector 4 to perform a treatment on the part to be treated after the position of the end effector 4 is determined in the first mode.

In the present embodiment, either of the first mode and the second mode is automatically selected based on a manipulation that the surgeon performs on the first manipulation unit 13.

The third mode shown in FIG. 4 is a mode for allowing the positional relationship between the surgical instrument 2, the instrument holder 6, the base link 7, and the link mechanism 8 shown in FIG. 2 to be changed only by a manipulation performed on the second manipulation unit 21. In the third mode, the position of the remote center RC can be changed. For example, in the third mode, setting of the remote center RC is canceled, then resetting of the remote center RC is performed with reference to the position of the trocar after the surgical instrument 2, the instrument holder 6, the base link 7, and the link mechanism 8 are moved to desired positions respectively to achieve a desired positional relationship between thereof. Changing the position of the remote center RC includes repositioning the trocar in a state in which the trocar is placed in the abdominal wall in the case of laparoscopic surgery or moving the surgical instrument 2 to a desired position in the case of abdominal surgery.

The third mode is used, for example, before a treatment starts or while a treatment is suspended in order to change an overall positional relationship of the surgical instrument 2, the instrument holder 6, the base link 7, and the link mechanism 8.

The fourth mode shown in FIG. 4 prohibits manipulation by the second manipulation unit 21. That is, the fourth mode turns the link adjustment modes off and allows the surgical instruments 2, the link mechanism 8, and the like to be moved only by the first manipulation unit 13.

The mode selection unit 33 shown in FIG. 3 selects one of the treatment mode and the link adjustment modes as a mode related to the first manipulation unit 13. The mode selection unit 33 selects one mode from the first mode, the second mode, the third mode, and the fourth mode shown in FIG. 4 as a mode related to the second manipulation unit 21. Conditions used for the mode selection unit 33 to select one mode from the plurality of control modes with regard to mode selection related to the second manipulation unit 21 include whether or not a manipulation is being performed using the first manipulation unit 13, whether or not a manipulation of constraining the position of the remote center RC or the position of the end effector 4 is being performed through the first manipulation unit, and whether or not the assistant is allowed to manipulate the second manipulation unit.

Figure 5:
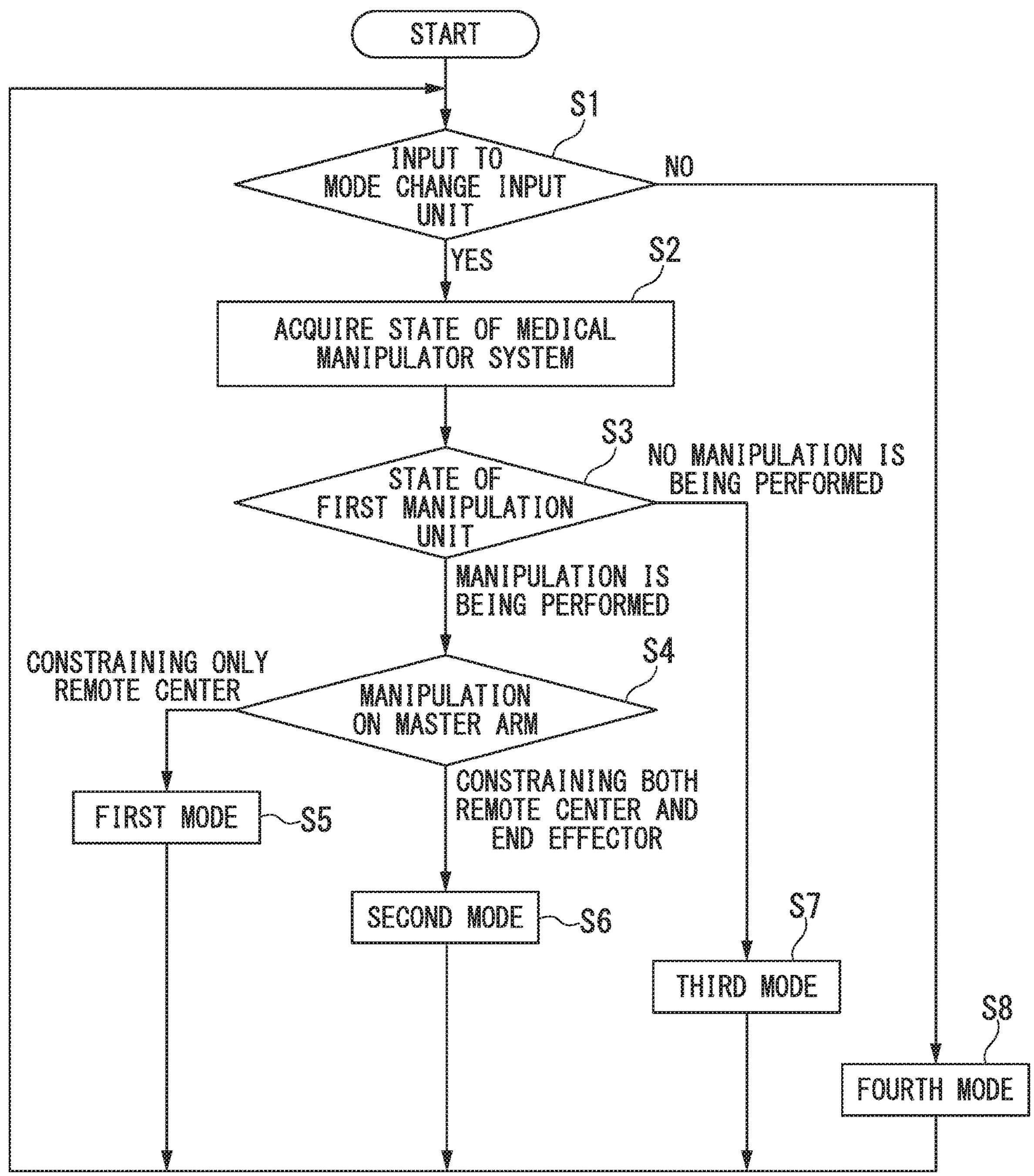
FIG. 5 is a flowchart showing an example of a control procedure of a control unit of the medical manipulator system.

FIG. 5 is a flowchart showing an example of a control procedure of the control unit of the medical manipulator system.

The control unit 30 selects one control mode while identifying the state of the medical manipulator system 1 in real time by repeating a process including the following step S1 to step S8.

Step S1 is a first step of determining the presence or absence of an input to the mode change input unit 22. In step S1, if there is no input to the mode change input unit 22, the process proceeds to step S8 of selecting the fourth mode and then returns to step S1. When an input to the mode change input unit 22 is detected in step S1, the process proceeds to step S2.

Step S2 is a second step of acquiring the state of the medical manipulator system 1. In step S2, the state acquisition unit 31 acquires and stores the state of the medical manipulator system 1. Here, step S2 is completed and the process proceeds to step S3.

Step S3 is a step of determining whether or not the first manipulation unit 13 is being manipulated. When it is determined based on information of the state stored by the state acquisition unit 31 that the first manipulation unit 13 is being manipulated in step S3, the process proceeds to step S4, and when it is determined that the first manipulation unit 13 is not being manipulated, the process proceeds to step S7 to select the third mode.

In step S4, it is determined whether the manipulation on the master arms 15 is a manipulation of constraining only the position of the remote center RC or a manipulation of constraining both the position of the remote center RC and the position of the end effector 4. When it is determined based on the information of the state stored by the state acquisition unit 31 that the manipulation on the master arms 15 is a manipulation of constraining only the position of the remote center RC in step S4, the process proceeds to step S5 to select the first mode. When it is determined that the manipulation on the master arms 15 is a manipulation of constraining both the position of the remote center RC and the position of the end effector 4, the process proceeds to step S6 to select the second mode.

Through repetitive operation of the process including steps S1 to S8, while the push button switch of the mode change input unit 22 is being pressed, the first mode, the second mode, or the third mode is selected such that the link mechanism 8 can be moved by the second manipulation unit 21. In the present embodiment, each step shown in the sequence of steps S3 to step S8 provides a third step of selecting one suitable mode based on the state of the medical manipulator system 1.

Since the link mechanism 8 of the medical manipulator system 1 of the present embodiment includes the redundant joint 10 in addition to the regular joint 9, the position and orientation of the surgical instrument 2 are maintained even if the link mechanism 8 is moved by the second manipulation unit 21. Furthermore, even while the link mechanism 8 is being moved by the second manipulation unit 21, the surgeon can continue a manipulation such as a treatment on the part to be treated or positioning of the end effector 4 since the regular joint 9 of the link mechanism 8 can operate according to manipulation by the first manipulation unit 13.

The movement of the medical manipulator system 1 of the present embodiment will now be described with reference to FIGS. 1 to 4.

After the medical manipulator system 1 is activated, the medical manipulator system 1 operates in a predetermined initialization mode to set initial positions of the surgical instrument 2, the instrument holder 6, the base link 7, and the link mechanism 8 with respect to the patient.

Subsequently, the surgeon observes a part to be treated with an endoscope. This endoscope is held by the instrument holder 6 in the same way as other surgical instruments 2 and the endoscope is connected to the medical manipulator system 1 to allow the monitor 14 of the first manipulation unit 13 to display an image of the part to be treated.

When the surgeon performs observation, treatment, or the like on the part to be treated, the surgeon can manipulate the endoscope or the surgical instrument 2 by pushing the foot switch 16 while viewing the monitor 14. The sensors 17 provided on the first manipulation unit 13 detect that the head of the surgeon is at the position of the monitor 14 and the sensors 17 also detect that there is an input to the foot switch 16. When the surgeon is manipulating the master arms 15, the sensors 17 detect that manipulation on the master arms 15 is being performed. The control unit 30 determines that the first manipulation unit 13 is being manipulated in accordance with such detection results of the sensors 17 and receives a manipulation command for the first manipulation unit 13.

The surgeon manipulates the endoscope or the surgical instrument 2 using the first manipulation unit 13 to observe the part to be treated and to perform a treatment on the part to be treated as needed.

In the case of performing a treatment on the part to be treated, the surgeon operates the master arms 15 of the first manipulation unit 13 while viewing the monitor 14 and the surgeon performs a treatment on the part to be treated using the end effector 4. At this time, in a state in which the assistant does not need to manually change the position and orientation of the link mechanism 8, no input is made to the mode change input unit 22 disposed on the second manipulation unit 21, and therefore the fourth mode is selected in the medical manipulator system 1 such that the link adjustment mode is turned off and the medical manipulator system 1 operates in the treatment mode.

Since the surgeon only views the monitor 14 while the surgeon is treating the part to be treated, the surgeon does not know how the link mechanisms 8 are operating. While the surgeon is treating the part to be treated, the assistant observes whether the link mechanisms 8 are about to interfere with each other or whether the link mechanisms 8 are about to collide with other medical instruments. In the present embodiment, the positions of the above-described medical instruments are not recognized by the medical manipulator system 1 and therefore, when the assistant has determined that there is a possibility that a link mechanism 8 will collide with a medical instrument, the assistant moves the medical instrument or moves the link mechanism 8.

In the present embodiment, when the assistant moves a link mechanism 8, the assistant pushes and pulls the link mechanism 8 while pushing a mode change input unit 22 (a push button switch) arranged on the link mechanism 8 to move the link mechanism 8 to a desired position. When the push button switch of the mode change input unit 22 is pushed, the control unit 30 specifies the link mechanism 8 to be changed from the fourth mode to another mode and unlocks the redundant joint 10 of the specified link mechanism 8 (i.e., terminates the fourth mode). When the fourth mode has been terminated, the regular joint 9 of the link mechanism 8 operates in accordance with manipulation by the first manipulation unit 13, and the redundant joint 10 of the link mechanism 8 operates following the push and pull of the second manipulation unit 21. Thus, when the fourth mode has been terminated in response to the input to the mode change input unit 22 in a state in which the first manipulation unit 13 is in use such that the surgeon is performing manipulation using the first manipulation unit 13, the control unit 30 operates in the first mode or the second mode according to manipulation on the master arms 15. Thus, the assistant can change the position and orientation of the link mechanism 8 within a range of degrees of freedom given by the redundant joint 10 among all degrees of freedom of the link mechanism 8.

Termination of manipulation on the second manipulation unit 21 is detected by the control unit 30 as the assistant who was manipulating the second manipulation unit 21 releases the push button switch of the mode change input unit 22. When the control unit 30 detects that there is no input to the push button switch, the mode selection unit 33 terminates the first mode or the second mode and shifts to the fourth mode. Thus, the control unit 30 controls the base link 7, the link mechanism 8, the instrument holder 6, and the surgical instrument 2 according to the fourth mode. In the fourth mode, the control unit 30 prohibits manipulation by the second manipulation unit 21. That is, when the fourth mode is selected, the control unit 30 locks the redundant joint 10. As a result, the medical manipulator system 1 enters a treatment mode in which the base link 7, the link mechanism 8, the instrument holder 6, and the surgical instrument 2 are manipulated only through manipulation by the first manipulation unit 13.

When the medical manipulator system 1 of the present embodiment is in use, a plurality of parts separated from each other may be subjected to treatment. In this case, an overall positional relationship between the surgical instrument 2, the instrument holder 6, the base link 7, and the link mechanism 8 may be changed in order to move the end effector 4 from one part to be treated to another part to be treated.

For example, when the end effector 4 is moved from one part to be treated to another part to be treated, the surgeon suspends manipulation on the first manipulation unit 13. That is, the surgeon releases his/her foot from the foot switch 16 and releases his/her hands from the master arms 15 and further moves his/her head away from the monitor 14 of the first manipulation unit 13. Upon completion of these three manipulations, the state acquisition unit 31 of the control unit 30 acquires and stores a state in which the first manipulation unit is not in use.

When the assistant performs an input on the mode change input unit 22 in a state in which the first manipulation unit is not in use, the mode selection unit 33 terminates the fourth mode and selects the third mode. This allows the control unit 30 to unlock the joint or the like of each part such that the surgical instrument 2, the instrument holder 6, the base link 7, and the regular joint 9 and the redundant joint 10 of the link mechanism 8 can operate according to manipulation on the second manipulation unit.

When the assistant who manipulates the second manipulation unit 21 finishes the manipulation, the assistant releases his/her hand from the mode change input unit 22. Accordingly, the third mode is terminated and the fourth mode is selected at the mode selection unit 33 such that the control unit 30 locks the joint or the like of each part of the surgical instrument 2, the instrument holder 6, the base link 7, and the regular joint 9 and the redundant joint 10 of the link mechanism 8. When the first manipulation unit 13 enters a state in which the first manipulation unit 13 is being manipulated, the joint or the like of each part of the surgical instrument 2, the instrument holder 6, the base link 7, and the regular joint 9 and the redundant joint 10 of the link mechanism 8 are allowed to operate according to manipulation on the first manipulation unit 13.

As described above, in the medical manipulator system 1 of the present embodiment, the mode change input unit 22 can be used as a switch between the first or second mode and the fourth mode when it is determined according to the state of the medical manipulator system 1 that the first manipulation unit 13 is in use and can be used as a switch between the third mode and the fourth mode when it is determined that the first manipulation unit 13 is not in use. That is, in the present embodiment, it is possible to select a suitable mode from the four modes, i.e., from the first to fourth modes, through alternative selection using the mode change input unit 22. As a result, according to the medical manipulator system 1 of the present embodiment, it is possible to easily perform an input manipulation for manually operating the link mechanism 8.

Second Embodiment

Figure 6:
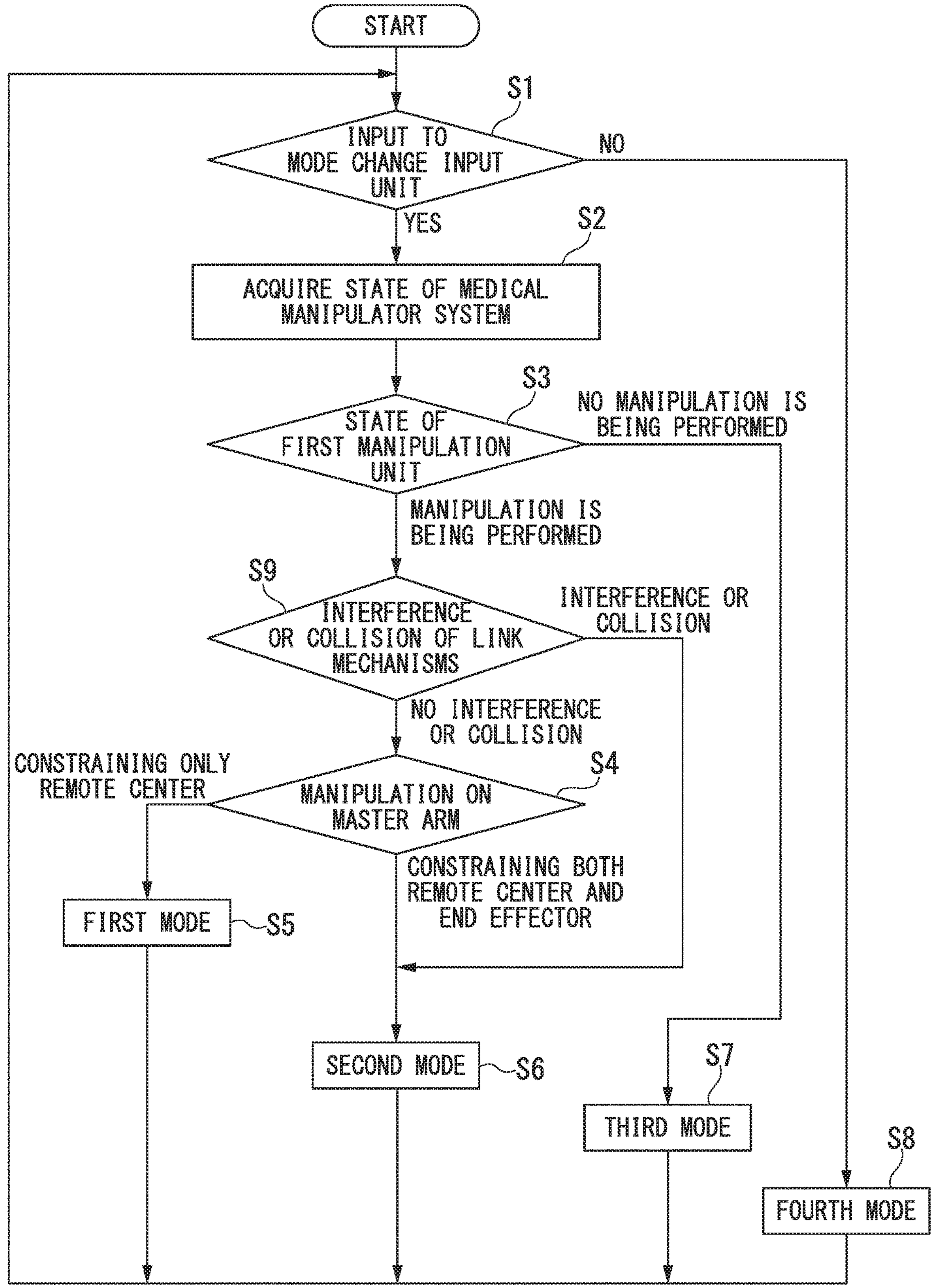
FIG. 6 is a flowchart showing an example of a control procedure of a control unit of a medical manipulator system according to a second embodiment of the present invention.

A second embodiment of the present invention will now be described. FIG. 6 is a flowchart showing an example of a control procedure of the control unit of the medical manipulator system of the present embodiment. In the present embodiment, constituent elements common to the first embodiment are denoted by the same reference signs (see FIGS. 1 to 3) as those of the first embodiment and duplicate description is omitted.

In the medical manipulator system 1 of the present embodiment, the control unit 30 performs control different from the first embodiment in cases such as when the link mechanisms 8 interfere with each other and when a link mechanism 8 collides with another medical instrument or the like.

In the control unit 30 of the present embodiment, the state acquisition unit 31 acquires interference between the link mechanisms 8 or collision between a link mechanism 8 and another object based on detection states of the force sensors 12.

For example, when the force sensors 12 have simultaneously detected the occurrence of interference or collision of the plurality of link mechanisms 8, the control unit 30 determines that interference of the link mechanisms 8 has occurred. The control unit 30 may specify interference between the link mechanisms 8 using both a positional relationship of the link mechanisms 8 and detection results of the force sensors 12 in combination.

When a force sensor 12 provided in one of the plurality of link mechanisms 8 has detected the occurrence of interference or collision, the control unit 30 determines that a link mechanism 8 corresponding to the force sensor 12 has collided with an object other than the link mechanisms 8 (such as a medical instrument or an assistant's body). The object other than the link mechanisms 8 may be any object located within a movable range of the medical manipulator system 1 other than those whose positions are previously recognized by the medical manipulator system 1 of the present embodiment.

The mode selection unit 33 specifies one mode from the first mode, the second mode, the third mode, and the fourth mode based on a state acquired by the state acquisition unit 31.

The present embodiment includes step S9 of branching the process based on the presence or absence of interference or collision of the link mechanisms 8 between step S3 and step S4 disclosed in the first embodiment.

In step S9, when it is determined that the state acquisition unit 31 stores information indicating that there is interference or collision of the link mechanisms 8, the process proceeds to step S6 to select the second mode. In step S9, when it is determined that the state acquisition unit 31 stores information indicating that there is no interference or collision of the link mechanisms 8, the mode selection unit 33 proceeds to step S4 and performs the process from step S4 onward, similar to the first embodiment.

In the present embodiment, in the case in which the state acquisition unit 31 has detected that there is interference or collision of the link mechanisms 8, regardless of the state of manipulation on the master arms 15, the second mode is selected when an input is made to the mode change input unit 22, and the assistant can perform a manipulation of removing the interference or collision of the link mechanisms 8 using the second manipulation unit 21.

In the present embodiment, when the second mode is selected, the manipulation of the first manipulation unit 13 is limited to a manipulation of constraining the position of the end effector 4 (without constraining the orientation and movement of the end effector 4). Therefore, when the link mechanisms 8 interfere with each other while a treatment is being performed on a part to be treated and thus the second mode is selected, the treatment can be continued using the first manipulation unit 13 in a range in which the position of the end effector 4 is not changed.

In the present embodiment, when the state acquisition unit 31 detects that there is interference or collision of the link mechanisms 8, the second mode is selected to prevent the link mechanisms 8 from operating to swing about the remote center RC and therefore it is easy to perform manipulation of the link mechanisms 8 using the second manipulation unit.

In the present embodiment, when the second mode is selected, both the regular joint 9 and the redundant joint 10 may also be allowed to be manipulated by the second manipulation unit 21 with the position and orientation of the surgical instrument 2 being fixed (with only the end effector 4 being operable). In this case, the degree of freedom of the link mechanism 8 is further increased, thereby making it much easier to remove interference and collision.

In the present embodiment, a case in which the link mechanisms 8 stop without collision or interference being able to be removed in the second mode is conceivable. In this case, control according to the third mode is performed in order to temporarily suspend the treatment, quickly resolve the interference or collision, and resume the treatment. The third mode is selected when it is determined in step S3 that the first manipulation unit 13 is not being manipulated, similar to the first embodiment.

As described above, according to the medical manipulator system 1 of the present embodiment, when interference or collision has occurred in the link mechanisms 8, it is possible to easily perform an input manipulation for manually operating the link mechanisms 8 while increasing the possibility of continuing the treatment.

When the surgeon who manipulates the first manipulation unit 13 has suspended the manipulation, the mode selection unit 33 automatically sets a mode to which switching is to be made from the fourth mode, such that switching is made to the third mode in which the link mechanism 8 can move with a higher degree of freedom than in the second mode. Therefore, it is possible to easily perform an input manipulation for manually operating the link mechanisms 8 even when, for example, complicated interference has occurred between the link mechanisms 8.

In the present embodiment, the case in which the third mode is selected is not limited to when interference or collision of the link mechanisms 8 has occurred and the third mode may also be selected when the part to be treated is changed from one part to be treated to another part to be treated, similar to the first embodiment described above.

In the embodiments described above, the control unit 30 can be realized by hardware such as one or more Central Processing Unit (CPU), and by reading instructions stored on a computer readable storage device.

Although preferred embodiments of the present invention have been described above, the present invention is not limited to the embodiments and modifications thereof. Additions, omissions, substitutions and other changes in the structure are possible without departing from the spirit of the present invention. The present invention is not limited by the foregoing description but is limited only by the scope of the appended claims.

What is claimed is:

1. A medical manipulator system comprising:
a plurality of end effectors configured to be controlled to perform a treatment;
a plurality of arms to which the plurality of end effectors are attached respectively,
wherein each of the plurality of arms comprises:
a plurality of movable parts;
a sensor configured to detect contact; and
a switch configured to be operated to permit movement of the plurality of movable parts by an external force, and
wherein the plurality of movable parts of the each of the plurality of arms are configured to be moved under one of a plurality of modes, wherein each of the plurality of modes comprises a combination of:
movement by one or more actuators; and
movement by the external force; and
a controller configured to:
control the plurality of end effectors to perform the treatment;
select the one of the plurality of modes; and
effect movement of the plurality of movable parts by controlling the one or more actuators and by permitting movement by the external force in accordance with the one of the plurality of modes selected,
wherein the controller is configured to, with respect to one arm of the plurality of arms:
determine that there is interference or collision with the one arm, by another arm of the plurality of arms, in response to the sensor of the one arm and the sensor of the another arm simultaneously detecting contact;
determine whether the switch is operated;
select a second mode of the plurality of modes in response to determining that there is the interference or collision with the one arm and determining that the switch is operated; and
in response to selecting the second mode:
control the one or more actuators to move a first group of the plurality of movable parts of the one arm while a position of a remote center of the one arm is fixed and while a position of the end effector of the one arm is fixed; and
permit movement of a second group of the plurality of movable parts of the one arm by the external force while the position of the remote center of the one arm is fixed and the position of the end effector of the one arm is fixed.

2. The medical manipulator system according to claim 1, wherein the controller is configured to, with respect to the one arm:
select a first mode of the plurality of modes in response to determining that there is no interference or collision with the one arm and determining that the switch is operated; and
in response to selecting the first mode:
control the one or more actuators to move the first group of the plurality of movable parts of the one arm while the position of the remote center of the one arm is fixed and while the position of the end effector of the one arm is not fixed; and
permit movement of the second group of the plurality of movable parts of the one arm by the external force while the position of the remote center of the one arm is fixed and while the position of the end effector of the one arm is not fixed.

3. The medical manipulator system according to claim 1, wherein the controller is configured to, with respect to the one arm:
receive a mode change input indicating the selection of a third mode of the plurality of modes; and
in response to receiving the mode change input indicating the selection of the third mode, permit movement of the plurality of movable parts of the one arm by only the external force.

4. The medical manipulator system according to claim 1, wherein the controller is configured to, with respect to the one arm:
receive a mode change input indicating the selection of a fourth mode; and
in response to receiving the mode change input indicating the selection of the fourth mode, control the one or more actuators to move the plurality of movable parts of the one arm based on a command issued based on manipulation of a master device.

5. The medical manipulator system according to claim 1, wherein the controller is further configured to determine that there is the interference or the collision with the one arm, by another object, in response to only the sensor of the one arm detecting contact.

6. A controller for controlling a medical manipulator system, the medical manipulator system comprising:
a plurality of end effectors configured to be controlled to perform a treatment; and
a plurality of arms to which the plurality of end effectors are attached respectively,
wherein each of the plurality of arms comprises:
a plurality of movable parts
a sensor configured to detect contact; and
a switch configured to be operated to permit movement of the plurality of movable parts by an external force, and
wherein the plurality of movable parts of the each of the plurality of arms are configured to be moved under one of a plurality of modes, wherein each of the plurality of modes comprises a combination of:
movement by one or more actuators; and
movement by the external force,
wherein the controller comprises one or more processors configured to:
control the plurality of end effector to perform the treatment;
select the one of the plurality of modes; and
effect movement of the plurality of movable parts by controlling the one or more actuators and by permitting movement by the external force in accordance with the one of the plurality of modes selected, wherein the one or more processors are configured to, with respect to one arm of the plurality of arms:

determine that there is interference or collision with the one arm, by another arm of the plurality of arms, in response to the sensor of the one arm and the sensor of the another arm simultaneously detecting contact;

determine whether the switch is operated;

select a second mode of the plurality of modes in response to determining that there is the interference or collision with the one arm and determining that the switch is operated; and in response to selecting the second mode:

control the one or more actuators to move a first group of the plurality of movable parts of the one arm while the position of a remote center of the one arm is fixed and while a position of the end effector of the one arm is fixed; and permit movement of a second group of the plurality of movable parts by the external force while the position of the remote center is fixed and the position of the end effector is fixed.

7. The controller according to claim 6, wherein the one or more processors are configured to, with respect to the one arm of the plurality of arms:

select a first mode in response to determining that there is no interference or collision with the one arm and determining that the switch is operated; and in response to selecting the first mode:

control the one or more actuators to move the first group of the plurality of parts of the one arm while the position of the remote center of the one arm is fixed and while the position of the end effector of the one arm is not fixed; and permit movement of the second group of the plurality of parts of the one arm by the external force while the position of the remote center of the one arm is fixed and while the position of the end effector of the one arm is not fixed.

8. The controller according to claim 6, wherein the one or more processors are configured to, with respect to the one arm of the plurality of arms:

receive a mode change input indicating the selection of a third mode of the plurality of modes; and in response to receiving the mode change input indicating the selection of the third mode, permit movement of the plurality of parts of the one arm by only the external force.

9. The controller according to claim 6, wherein the one or more processors are configured to, with respect to the one arm:

receive a mode change input indicating the selection of a fourth mode of the plurality of modes; and in response to receiving the mode change input indicating the selection of the fourth mode, control the one or more actuators to move the plurality of movable parts of the one arm based on a command issued based on manipulation of a master device.

10. The controller according to claim 6, wherein the one or more processors are further configured to determine that there is the interference or the collision with the one arm, by another object, in response to only the sensor of the one arm detecting contact.

11. A non-transitory computer-readable storage medium storing instructions for controlling a medical manipulator system, the medical manipulator system comprising:

a plurality of end effectors configured to be controlled to perform a treatment; and a plurality of arms to which the plurality of end effectors are attached respectively, wherein each of the plurality of arms comprises:

a plurality of movable parts;

a sensor configured to detect contact; and a switch configured to be operated to permit movement of the plurality of movable parts by an external force, and wherein the plurality of movable parts of the each of the plurality of arms are configured to be moved under one of a plurality of modes, wherein each of the plurality of modes comprises a combination of:

movement by one or more actuators; and movement by the external force, wherein the instructions cause a computer to perform processes comprising:

controlling the plurality of end effectors to perform the treatment;

selecting the one of the plurality of modes; and effecting movement of the plurality of movable parts by controlling the one or more actuators and by permitting movement by the external force in accordance with the one of the plurality of modes selected, wherein the instructions cause the computer to perform process comprising, with respect to one arm of the plurality of arms:

determining that there is the interference or collision with the one arm, by another arm of the plurality of arms, in response to the sensor of the one arm and the sensor of the another arm, simultaneously detecting contact;

selecting a second mode of the plurality of modes in response to determining that there is the interference or collision with the one arm and determining that the switch is operated; and in response to selecting the second mode:

controlling the one or more actuators to move a first group of the plurality of movable parts of the one arm while a position of a remote center of the one arm is fixed and while a position of the end effector of the one arm is fixed; and permitting the movement of a second group of the plurality of movable parts of the one arm by the external force while the position of the remote center of the one arm is fixed and the position of the end effector of the one arm is fixed.

12. The non-transitory computer-readable storage medium according to claim 11, wherein the instructions cause the computer to perform processes comprising, with respect to the one arm:

selecting a first mode of the plurality of modes in response to determining that there is no interference or collision with the one arm and determining that the switch is operated; and in response to selecting the first mode:

controlling the one or more actuators to move the first group of the plurality of parts of the one arm while the position of the remote center of the one arm is fixed and while the position of the end effector of the one arm is not fixed; and permitting movement of the second group of the plurality of parts of the one arm by the external force while the position of the remote center of the one arm is fixed and while the position of the end effector of the one arm is not fixed.

13. The non-transitory computer-readable storage medium device according to claim 11, wherein the instructions cause the computer to perform processes comprising, with respect to the one arm:

receiving a mode change input indicating the selection of a third mode of the plurality of modes; and in response to receiving the mode change input indicating the selection of the third mode, permitting movement of the plurality of parts of the one arm by only the external force.

14. The non-transitory computer-readable storage medium according to claim 11, wherein the instructions cause the computer to perform processes comprising, with respect to the one arm:

receiving a mode change input indicating the selection of a fourth mode of the plurality of modes; and in response to receiving the mode change input indicating the selection of the fourth mode, controlling the one or more actuators to move the plurality of movable parts of the one arm based on a command issued based on manipulation of a master device.

15. The non-transitory computer-readable storage medium according to claim 11, wherein the instructions cause the computer to perform processing comprising determining that there is the interference or the collision with the one arm, by another object, in response to only the sensor of the one arm detecting contact.

* * * * *